US006723340B2

(12) United States Patent
Gusler et al.

(10) Patent No.: US 6,723,340 B2
(45) Date of Patent: Apr. 20, 2004

(54) OPTIMAL POLYMER MIXTURES FOR GASTRIC RETENTIVE TABLETS

(75) Inventors: Gloria Gusler, Cupertino, CA (US); Bret Berner, El Granada, CA (US); Mei Chau, Sunnyvale, CA (US); Aimee Padua, Daly City, CA (US)

(73) Assignee: DepoMed, Inc., Menlo Park, CA (US)

( * ) Notice: Subject to any disclaimer, the term of this patent is extended or adjusted under 35 U.S.C. 154(b) by 0 days.

(21) Appl. No.: 10/029,134

(22) Filed: Oct. 25, 2001

(65) Prior Publication Data

US 2003/0104053 A1 Jun. 5, 2003

(51) Int. Cl.[7] ............ A61K 9/22; A61K 47/34; A61K 47/38
(52) U.S. Cl. ............ 424/468; 424/486; 424/488
(58) Field of Search ............ 424/486, 480, 424/468, 488; 514/866, 635, 722.3, 781

(56) References Cited

U.S. PATENT DOCUMENTS

| 4,404,183 A | 9/1983 | Kawata et al. |
| 4,915,952 A | 4/1990 | Ayer et al. |
| 5,273,758 A | 12/1993 | Royce |
| 5,328,942 A | 7/1994 | Akhtar et al. |
| 5,451,409 A | 9/1995 | Rencher et al. |
| 5,783,212 A | 7/1998 | Fassihi et al. |
| 5,945,125 A | 8/1999 | Kim |
| 5,972,389 A | 10/1999 | Shell et al. |
| 6,090,411 A | 7/2000 | Pillay et al. |
| 6,120,803 A | 9/2000 | Wong et al. |
| 6,210,710 B1 | 4/2001 | Skinner |
| 6,217,903 B1 | 4/2001 | Skinner |
| 6,361,795 B1 | 3/2002 | Kuczynski et al. |

FOREIGN PATENT DOCUMENTS

| GB | 1 330 829 | 9/1973 |
| WO | WP 97/18814 A1 | 5/1997 |

OTHER PUBLICATIONS

Peh, K. et al., "Polymeric Files as Vehicle for Buccal Delivery: Swelling, Mechanical, and Bioadhesive Properties." J Pharm Pharmaceut Sci (www.ualberta.ca/~csps) 2 (2): 53–61, (Aug. 1999).

Sriwongjanya, M., "Effect of ion exchange resins on the drug release from matrix tablets." European Journal of Pharmaceutics and Biopharmaceutics 46. pp. 321–327 (Nov. 1998).

Baichwal, A. and Neville, D.A. "Culturing Innovation and Enhancing Medications Using Oral Drug Delivery," *Drug Delivery Technology* May 2002, pp. 65–68, vol. 2, No. 3.

Halsas, M. et al. "Biopharmaceutical Evaluation of Time–Controlled Press–Coated Tablets Containing Polymers to Adjust Drug Release," *Eur. J. Drug Metab. Pharmacokinet.* Apr.–Jun. 1998, pp. 190–196, vol. 23, No. 2.

Sirkiä, T. et al. "Biopharmaceutical Evaluation of New Prolonged–Release Press–Coated Ibuprofen Tablets Containing Sodium Alginate to Adjust Drug Release," *International J. Pharmaceutics* 1994, pp. 179–187, vol. 107.

(List continued on next page.)

*Primary Examiner*—Edward J. Webman
(74) *Attorney, Agent, or Firm*—M. Henry Heines; Townsend and Townsend and Crew LLP (57) ABSTRACT

Unit dosage form tablets for the delivery of pharmaceuticals are formed of the pharmaceutical dispersed in a solid unitary matrix that is formed of a combination of poly(ethylene oxide) and hydroxypropyl methylcellulose. The combination offers unique benefits in terms of release rate control and reproducibility while allowing both swelling of the tablet to effect gastric retention and gradual disintegration of the tablet to clear the tablet from the gastrointestinal tract after release of the drug has occurred.

19 Claims, 3 Drawing Sheets

OTHER PUBLICATIONS

Sirkiä, T. et al. "Development and Biopharmaceutical Evaluations of a New Press–Coated Prolonged–Release Salbutamol Sulphate Tablet in Man," *Eur. J. Pharm. Sci.* 1994, pp. 195–201, vol. 1.

Ranga Rao, K.V. and K. Padmalatha Devi; "Swelling controlled–release systems: recent developments and applications"; *International Journal of Pharmaceutics*; 1988; pp. 1–13; vol. 48; Elsevier Science Publishers.

Pillay, Viness and Reza Fassihi; "Electrolyte–Induced Compositional Heterogeneity: A Novel Approach for Rate–Controlled Oral Drug Delivery"; *Journal of Pharamceutical Sciences*; Nov. 1999; pp. 1140–1148; vol. 88, No. 11.

Pillay, Viness and Reza Fassihi; "In situ electrolyte interactions in a disk–compressed configuration system for up–curving and constant drug delivery"; *Journal of Controlled Release*; 2000; pp. 55–65; vol. 67; Elsevier Science.

Maggi, L. et al.; "High molecular weight polyethylene oxides (PEOs) as an alternative to HPMC in controlled release dosage forms"; *International Journal of Pharmaceutics*; 2000; pp. 229–238; vol. 195; Elsevier Science.

U.S. Patent Application 10/152,914; "Method of Treating Gastroesophageal Reflux Disease and Nocturnal Acid Breakthrough"; May 20, 2002.

Figure 6

OPTIMAL POLYMER MIXTURES FOR GASTRIC RETENTIVE TABLETS

BACKGROUND OF THE INVENTION

1. Field of the Invention

This invention arises in the technology of pharmaceutical dosage forms, and relates in particular to formulations for drugs that benefit from a prolonged time of controlled release in the stomach and upper gastrointestinal (GI) tract, and from an enhanced opportunity for absorption in the stomach and upper GI tract rather than the lower portions of the GI tract.

2. Description of the Prior Art

Many drugs have their greatest therapeutic effect when released in the stomach, particularly when the release is prolonged in a continuous, controlled manner. Drugs delivered in this manner have fewer side effects and produce their therapeutic effect without the need for repeated or frequent dosing. Localization of the drug delivery in the stomach is an advantage for the treatment of local disorders of the stomach such as esophageal reflux disease, for the eradication of ulcer-causing bacteria in the gastric mucosa, and for the treatment of disorders that require sustained antacid action. Sustained release in the stomach is also useful for therapeutic agents that the stomach does not readily absorb, since sustained release prolongs the contact time of the agent in the stomach or in the upper part of the small intestine, which is where absorption occurs and contact time is limited.

In the normal digestive process, the passage of matter through the stomach is delayed by a physiological condition that is variously referred to as the digestive mode, the postprandial mode, or the "fed mode." Between fed modes, the stomach is in the interdigestive or "fasting" mode. The difference between the two modes lies in the pattern of gastroduodenal motor activity.

In the fasting mode, the stomach exhibits a cyclic activity called the interdigestive migrating motor complex (IMMC). This activity occurs in four phases:

- Phase I, which lasts 45 to 60 minutes, is the most quiescent, with the stomach experiencing few or no contractions.
- Phase II is characterized by sweeping contractions occurring in a irregular intermittent pattern and gradually increasing in magnitude.
- Phase III consists of intense bursts of peristaltic waves in both the stomach and the small bowel. This lasts for 5 to 15 minutes.
- Phase IV is a transition period of decreasing activity which lasts until the next cycle begins.

The total cycle time for all four phases is approximately 90 minutes. The greatest activity occurs in Phase III whose powerful peristaltic waves sweep the swallowed saliva, gastric secretions, food particles, and particulate debris, out of the stomach and into the small intestine and colon. Phase III thus serves as an intestinal housekeeper, preparing the upper tract for the next meal and preventing bacterial overgrowth.

The fed mode is initiated by nutritive materials entering the stomach upon the ingestion of food. Initiation is accompanied by a rapid and profound change in the motor pattern of the upper gastrointestinal (GI) tract, over a period of 30 seconds to one minute. The change is observed almost simultaneously at all sites along the GI tract and occurs before the stomach contents have reached the distal small intestine. Once the fed mode is established, the stomach generates 3–4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

The particle size required for gastric retention during the fasting mode is substantially larger than the particle size required for gastric retention in the fed mode. Particles large enough to be retained in the fasting mode are too large for practical administration in most patients. Particles of a smaller particle size can be retained in the stomach if they are administered to a patient who is in the fed mode, and this offers a means of prolonging the amount of time that the particles spend in the stomach.

The prior art of dosage forms for gastric retention also teaches that the residence time of drug formulation particles in the stomach can be prolonged by using particles that are small enough to be swallowed comfortably but swell to a larger size upon contact with the gastric fluid in the stomach. With a great enough degree of swelling, particles of this type achieve gastric retention regardless of whether the subject is in the fed mode or the fasting mode. One means of achieving a swellable particle is to disperse the drug in a solid matrix formed of a substance that absorbs the gastric fluid and swells as a result of the absorbed fluid. Disclosures of this type of particle are found in U.S. Pat. No. 5,007,790 ("Sustained-Release Oral Drug Dosage Form;" Shell, inventor; Apr. 16, 1991), U.S. Pat. No. 5,582,837 ("Alkyl-Substituted Cellulose-Based Sustained-Release Oral Drug Dosage Forms;" Shell, inventor: Dec. 10, 1996): U.S. Pat. No. 5,972,389 ("Gastric-Retentive Oral Drug Dosage Forms for the Controlled Release of Sparingly Soluble Drugs and Insoluble Matter;" Shell et al., inventors; Oct. 26, 1999); and International (PCT) Patent Application WO 98/55107 ("Gastric-Retentive Oral Drug Dosage Forms for Controlled Release of Highly Soluble Drugs;" Shell et al., inventors; publication date Dec. 10, 1998).

Polymer matrices have also been used to achieve controlled release of the drug over a prolonged period of time. Such sustained or controlled release is achieved either by limiting the rate by which the surrounding gastric fluid can diffuse through the matrix and reach the drug, dissolve the drug and diffuse out again with the dissolved drug, or by using a matrix that slowly erodes, continuously exposing fresh drug to the surrounding fluid. Disclosures of polymer matrices that function by either of these two methods are found in U.S. Patent No. 6,210,710, ("Sustained release polymer blend for pharmaceutical applications," Skinner, inventor, Apr. 3, 2001); U.S. Pat. No. 6,217,903, ("Sustained release polymer blend for pharmaceutical applications," Skinner, inventor, Apr. 17, 2001); International (PCT) Patent Application WO 97/18814 (Pharmaceutical Formulations," MacRae et al., inventors, publication date May 29, 1997); U.S. Pat. No. 5,451,409, ("Sustained release matrix system using hydroxyethyl cellulose and hydroxypropyl cellulose polymer blends," Rencher et al., inventors, Sep. 19, 1995); U.S. Patent No. 5,945,125, ("Controlled release tablet," Kim, inventor, Aug. 31, 1999); International (PCT) Patent Application WO 96/26718 ("Controlled Release Tablet," Kim, inventor: publication date Sep. 6, 1996); U.S. Pat. No. 4,915,952, ("Composition comprising drug, HPC, HPMC, and PEO," Ayer et al., inventors, Apr. 10, 1990); U.S. Pat. No. 5,328,942, ("Seed film compositions," Akhtar et al., inventors, Jul. 12, 1994); U.S. Pat. No. 5,783,212, ("Controlled release drug delivery system," Fassihi et al., inventors, Jul. 21, 1998); U.S. Pat. No. 6,120,803, ("Prolonged release active agent dosage form for gastric retention," Wong et al., inventors, Sep. 19, 2000); U.S. Pat. No. 6,090,411, ("Monolithic tablet for controlled drug release," Pillay et al., inventors, Jul. 18, 2000).

The goals of gastric retention and controlled release are not always compatible. Poly(ethylene oxide) is a matrix material that possesses both swelling and controlled release properties, but at the amounts needed for high drug dosage, and particularly the amounts needed for sufficient swelling to achieve gastric retention, the use of poly(ethylene oxide) raises regulatory concerns, since the United States Food and Drug Administration lists poly(ethylene oxide) as a substance with undefined toxicology considerations when used at sufficiently high doses on a long-term basis. Other matrix materials swell but also offer the benefit of a more even and generally faster erosion in the gastric environment so that the dosage forms can clear the GI tract more predictably after a few hours of drug release. One such material is hydroxypropyl methylcellulose, which swells but not to the same degree as poly(ethylene oxide). Hydroxypropyl methylcellulose is not considered a toxicology risk at any level by the FDA. A disadvantage of matrices that erode more readily however is that they cause a high initial burst of drug release and a lower degree of control over the drug release rate over the initial course of the drug release.

SUMMARY OF THE INVENTION

It has now been discovered that the use of poly(ethylene oxide) and hydroxypropyl methylcellulose in combination as a matrix for a swellable, sustained-release tablet provides unexpectedly beneficial performance, avoiding or substantially reducing the problems enumerated above and offering improved control and reliability while retaining both the ability to swell for gastric retention and to control drug release. The swelling behavior of poly(ethylene oxide) is retained but balanced against the erosion behavior of hydroxypropyl methylcellulose which modulates the extent and progress of swelling. In certain preferred embodiments of the invention, despite the relatively low level of poly (ethylene oxide), the tablet increases to about 120% of its original weight within the first 30 minutes of contact with gastric fluid and continues to increase in size, reaching at least about 90% of its maximum weight or size within 8 hours and remaining in a swollen state for sufficient time to provide gastric retention. The competing yet complementary actions of swelling and erosion also provide the tablet with greater mechanical integrity so that it disintegrates more slowly and more evenly than tablets with poly(ethylene oxide) as the sole or primary matrix material. By offering a more reproducible erosion rate, the combined-polymer matrix tablet provides greater reproducibility in the drug release rate and transit time through the GI tract while still retaining the swelling behavior that results in gastric retention. A particular benefit of the combined-polymer matrices of this invention is that they provide a tablet with the swelling behavior of poly(ethylene oxide) while maintaining the level of poly(ethylene oxide) below any levels that encounter regulatory obstacles that have been established in view of certain recognized or perceived toxicological effects of poly(ethylene oxide).

The combined-polymer matrices of the present invention offer benefits to drugs ranging from highly soluble drugs whose delivery from the matrix occurs primarily by diffusion out of the matrix after being dissolved by the gastric fluid, to sparingly soluble drugs whose delivery from the matrix occurs primarily by erosion of the matrix. For the highly soluble drugs, the poly(ethylene oxide) component of the matrix limits the initial release of the drug and imparts gastric retention through swelling, while the hydroxypropyl methylcellulose component lowers the amount of poly(ethylene oxide) required while still allowing the swelling to occur. For the sparingly soluble drugs, the hydroxypropylmethyl cellulose component prevents premature release of the drugs by retarding the erosion rate of the poly(ethylene oxide) while the poly(ethylene oxide) provides superior gastric retention. For both high and low solubility drugs, therefore, and for drugs of intermediate solubilities as well, the two polymers function in a complementary manner, benefiting in terms of gastric retention and sustained drug release.

These and other features, advantages, applications and embodiments of the invention are described in more detail below.

DETAILED DESCRIPTION OF THE INVENTION AND PREFERRED EMBODIMENTS

Poly(ethylene oxide), also referred to herein as "polyethylene oxide" and "PEO," is a linear polymer of unsubstituted ethylene oxide. Poly(ethylene oxide) polymers having viscosity-average molecular weights of about 100,000 daltons and higher can be used. Examples of poly(ethylene oxide)s that are commercially available are:

POLYOX® NF, grade WSR Coagulant, molecular weight 5 million

POLYOX® grade WSR 301, molecular weight 4 million

POLYOX® grade WSR 303, molecular weight 7 million

POLYOX® grade WSR N-60K, molecular weight 2 million

These particular polymers are products of Dow Chemical Company, Midland, Mich., USA. Other examples exist and can likewise be used.

Celluloses are linear polymers of anhydroglucose, and hydroxypropyl methylcellulose, also referred to herein as "HPMC," is an anhydroglucose in which some of the hydroxyl groups are substituted with methyl groups to form methyl ether moieties, and others are substituted with hydroxypropyl groups or with methoxypropyl groups to form hydroxypropyl ether or methoxypropyl ether moieties. Examples of hydroxypropyl methylcelluloses that are commercially available are METHOCEL E (USP type 2910), METHOCEL F (USP type 2906), METHOCEL J (USP type 1828), METHOCEL K (USP type 2201), and METHOCEL 310 Series, products of The Dow Chemical Company, Midland, Mich., USA, the different products varying slightly in the degree of methoxyl and hydroxypropyl substitution. The average degree of methoxyl substitution in these products ranges from about 1.3 to about 1.9 (of the three positions on each unit of the cellulose polymer that are available for substitution) while the average degree of hydroxypropyl substitution per unit expressed in molar terms ranges from about 0.13 to about 0.82.

The choice of a particular molecular weight range for either the poly(ethylene oxide) or the hydroxypropyl methylcellulose can vary with the solubility of the drug contained in the tablet. Drugs of relatively high solubility will tend to be released more quickly by diffusion through the matrix than by erosion of the matrix, and this can be controlled by using polymers of relatively high molecular weights since the higher molecular weight will lessen the rate of outward diffusion of the drug. Drugs of lower solubilities will require a greater reliance on erosion of the matrix for release and will thus benefit from polymers of lower molecular weights which tend to erode more quickly. Thus for drugs of high solubility, preferred poly(ethylene oxide)s are those whose molecular weights, expressed as viscosity average molecular weights, range from about 2,000,000 to about 10,000,000, and most preferably from about 4,000,000 to about 7,000,000. The size of a hydroxypropyl methylcellulose polymer is expressed not as molecular weight but instead in terms of its viscosity as a 2% solution by weight in water. For drugs of high solubility, the preferred hydroxypropyl methylcellulose polymers are those whose viscosity is within the range of about 4,000 to about 200,000, more preferably from about 50,000 centipoise to about 200,000 centipoise, and most preferably from about 80,000 centipoise to about 120,000 centipoise.

Accordingly, for drugs of low solubility, preferred poly(ethylene oxide)s are those whose viscosity average molecular weights range from about 100,000 to about 5,000,000, and most preferably from about 500,000 to about 2,500,000, while preferred hydroxypropyl methylcellulose polymers are those whose viscosity is within the range of about 1,000 centipoise to about 100,000 centipoise, and most preferably from about 4,000 centipoise to about 30,000 centipoise.

It will be noted that some of the ranges cited above for high solubility drugs overlap or are contiguous (share a limit) with the some of the ranges for low solubility drugs. While "high solubility" and "low solubility" are terms whose meaning will be understood by those skilled in the art of pharmaceutical drugs, the terms are relative by nature, and the overlapping portions refer to drugs that are intermediate in solubility, i.e., "high solubility" drugs that are close to the "low solubility" range and vice versa.

The relative amounts of PEO and HPMC may vary within the scope of the invention and are not critical. In most cases, best results will be obtained with a PEO:HPMC weight ratio within the range of from about 1:3 to about 3:1, and preferably within the range of from about 1:2 to about 2:1. As for the total amount of polymer relative to the entire tablet, this may vary as well and will depend on the desired drug loading. In most cases, the polymer combination will constitute from about 15% to about 90% by weight of the dosage form, preferably from about 30% to about 65%, and most preferably from about 40% to about 50%. As noted above, the PEO content of the matrix can be maintained below the maximum dose established by the FDA (270 mg per tablet), and still achieve the beneficial effects of this invention. Accordingly, the PEO content of the tablet as a whole is preferably less than 270 mg, and more preferably less than 250 mg.

Drugs of relatively high solubility are generally considered to be those whose solubility in water at 37° C. is greater than one part by weight of the drug in twenty parts by weight of water. An alternative and preferred definition is those drugs whose solubility in water at 37° C. is greater than one part by weight of the drug in ten parts by weight of water, and a further alternative and even more preferred definition is those drugs whose solubility in water at 37° C. is greater than one part by weight of the drug in three parts by weight of water. Examples of drugs of high solubility are metformin hydrochloride, gabapentin, losartan potassium, vancomycin hydrochloride, captopril, erythromycin lactobionate, ranitidine hydrochloride, sertraline hydrochloride, ticlopidine hydrochloride, tramadol, fluoxetine hydrochloride, bupropion, lisinopril, iron salts, sodium valproate, valproic acid, and esters of ampicillin. Drugs of relatively low solubility are generally considered to be those whose solubility in water at 37° C. is from about 0.005% to about 5% by weight, and preferably those whose solubility in water at 37° C. is from about 0.01% to about 5% by weight. Examples of drugs of low solubility are cefaclor, ciprofloxacin (and its hydrochloride salt), saguinavir, ritonavir, nelfinavir, clarithromycin, azithromycin, ceftazidine, cyclosporin, digoxin, paclitaxel, and ketoconazole. Other drugs that can be dispersed in the combined-polymer matrix of this invention to achieve the beneficial effects discussed herein will be apparent to those skilled in the art.

Tablets in accordance with this invention can be prepared by common tabletting methods that involve mixing, comminution, and fabrication steps commonly practiced by and well known to those skilled in the art of manufacturing drug formulations. Examples of such techniques are:

(1) Direct compression using appropriate punches and dies, typically fitted to a suitable rotary tabletting press;

(2) Injection or compression molding;

(3) Granulation by fluid bed, by low or high shear granulation, or by roller compaction, followed by compression; and (4) Extrusion of a paste into a mold or to an extrudate to be cut into lengths.

When tablets are made by direct compression, the addition of lubricants may be helpful and is sometimes important to promote powder flow and to prevent breaking of the tablet when the pressure is relieved. Examples of typical lubricants are magnesium stearate (in a concentration of from 0.25% to 3% by weight, preferably about 1% or less by weight, in the powder mix), stearic acid (0.5% to 3% by weight), and hydrogenated vegetable oil (preferably hydrogenated and refined triglycerides of stearic and palmitic acids at about 1% to 5% by weight, most preferably about 2% by weight).

Additional excipients may be added as granulating aids (low molecular weight HPMC at 2–5% by weight, for example), binders (microcrystalline cellulose, for example), and additives to enhance powder flowability, tablet hardness, and tablet friability and to reduce adherence to the die wall. Other fillers and binders include, but are not limited to, lactose (anhydrous or monohydrate), maltodextrins, sugars, starches, and other common pharmaceutical excipients. These additional excipients may constitute from 1% to 50% by weight, and in some cases more, of the tablet.

The dosage forms of the present invention find utility when administered to subjects who are in either the fed mode or the fasting mode. Administration during the fed mode is preferred, since the narrowing of the pyloric opening that occurs in the fed mode serves as a further means of promoting gastric retention by retaining a broader size range of the dosage forms.

The fed mode is normally induced by food ingestion, but can also be induced pharmacologically by the administration of pharmacological agents that have an effect that is the same or similar to that of a meal. These fed-mode inducing agents may be administered separately or they may be included in the dosage form as an ingredient dispersed in the dosage form or in an outer immediate release coating. Examples of pharmacological fed-mode inducing agents are disclosed in co-pending U.S. patent application Ser. No. 09/432,881, filed Nov. 2, 1999, entitled "Pharmacological Inducement of the Fed Mode for Enhanced Drug Administration to the Stomach," inventors Markey, Shell, and Berner, the contents of which are incorporated herein by reference.

In certain embodiments of this invention, the tablet is in two (or more) layers, a first layer serving primarily to provide the swelling the results in gastric retention while a second layer serves primarily as a reservoir for the drug. The combined-polymer matrix of the present invention may be used in either or both of the two layers.

In certain further embodiments of this invention, the dosage form may contain additional drug in a quickly dissolving coating on the outer surface of the tablet. This may be the same drug as the drug in the matrix or a different drug. The coating is referred to as a "loading dose" and its purpose is to provide immediate release into the patient's bloodstream upon ingestion of the dosage form without first requiring the drug to diffuse through the polymer matrix. An optimal loading dose is one that is high enough to quickly raise the blood concentration of the drug but not high enough to produce the transient overdosing that is characteristic of highly soluble drugs that are not administered in controlled-release formulations.

A film coating may also be included on the outer surface of the dosage form for reasons other than a loading dose. The coating may thus serve an aesthetic function or a protective function, or it may make the dosage form easier to swallow or mask the taste of the drug.

The following examples are offered for purposes of illustration and are not intended to limit the invention.

EXAMPLE 1

This example illustrates the preparation of tablets of ciprofloxacin hydrochloride monohydrate in accordance with the invention, and compares the combination of PEO and hydroxypropyl methyl cellulose (HPMC) with PEO alone and HPMC alone in terms of the release profile of the drug and the swelling behavior, both over time and both in simulated gastric fluid (0.1 N HCl).

Tablets were formulated by dry blending a granulation of ciprofloxacin hydrochloride and poly(vinyl pyrrolidone) and the remaining excipients listed below, followed by pressing on a Carver "Auto C" tablet press (Fred Carver, Inc., Ind.). Specifications for the ingredients were as follows:

- ciprofloxacin hydrochloride monohydrate (the "Active Ingredient")
- poly(vinyl pyrrolidone) ("PVP," grade K29–32, manufactured by ISP)
- poly(ethylene oxide) ("PEO," grade PolyOx Coagulant, NF FP grade, manufactured by Union Carbide, a wholly owned subsidiary of Dow Chemical Company)
- hydroxypropylmethylcellulose ("K100M," grade Methocel K100M, having a viscosity of 100,000 cps as a 2% aqueous solution, premium, that meets the specification for type USP 2208 HPMC, manufactured by Dow Chemical Company)
- micro-crystalline cellulose ("MCC," type Avicel PH 101, manufactured by FMC Corporation)
- magnesium stearate ("M. St.")

The tablets were 1000 mg in size, and the pressing procedure involved a 0.7086"×0.3937" Mod Oval die (Natoli Engineering), using 4000 lbs force, zero second dwell time (the setting on the Carver press), and 100% pump speed.

Three lots of tablets were prepared, with the following compositions, all in weight percents (Lot B representing the combination of the present invention):

TABLE 1.1

Ciprofloxacin Tablet Composition

| Lot | % Active | % PVP | % PEO | % MCC | % K100M | % M. St. |
|-----|----------|-------|-------|-------|---------|----------|
| A | 58.2 | 4.38 | 32.42 | 5.01 | 0 | 0 |
| B | 57.6 | 4.34 | 19.99 | 4.95 | 12.11 | 0.99 |
| C | 57.6 | 4.34 | 0 | 4.95 | 32.10 | 0.99 |

Cumulative dissolution profiles were obtained in USP apparatus I (40 mesh baskets), 100 rpm, in 0.1 N HCl, by taking 5-mL samples without media replacement, at 15 minutes, 30 minutes, and 1, 2, 4, 6, and 8 hours. The profiles, based on the theoretical percent active added to the formulation, are shown in Table 1.2 and plotted in FIG. 1, in which the diamonds represent Lot A, the squares represent Lot B, and the triangles represent Lot C.

TABLE 1.2

Ciprofloxacin Cumulative Dissolution Profiles
Cumulative % Active Released

| Lot | 0.25 h | 0.5 h | 1 h | 2 h | 4 h | 6 h | 8 h |
|-----|--------|-------|-----|-----|-----|-----|-----|
| A | 1.40 | 2.25 | 3.96 | 7.41 | 14.89 | 19.33 | 24.33 |
| B | 1.43 | 2.28 | 3.56 | 6.56 | 13.30 | 17.23 | 21.74 |
| C | 1.44 | 2.16 | 3.59 | 6.14 | 11.30 | 13.71 | 15.85 |

Figure 1:
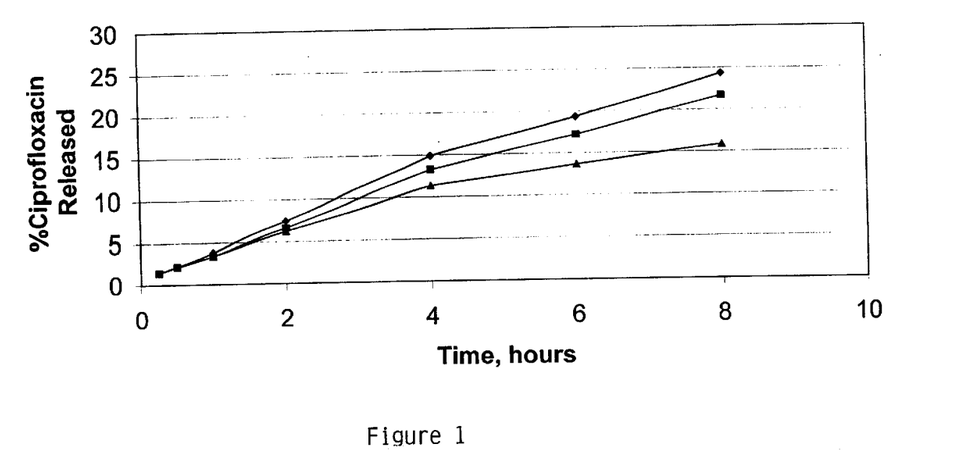
FIG. 1 is a plot showing the cumulative release of ciprofloxacin hydrochloride from tablets (as a percent of the total amount originally present in each tablet) in a gastric environment over time, comparing a polymer matrix consisting of a combination of PEO and HPMC to polymer matrices consisting of PEO and HPMC alone.

The dissolution profiles for this partially erosional tablet demonstrate that the combination of PEO and HPMC has a dissolution profile that is intermediate between those of PEO alone and HPMC alone and shows greater control over the drug release than the PEO alone.

Figure 2:
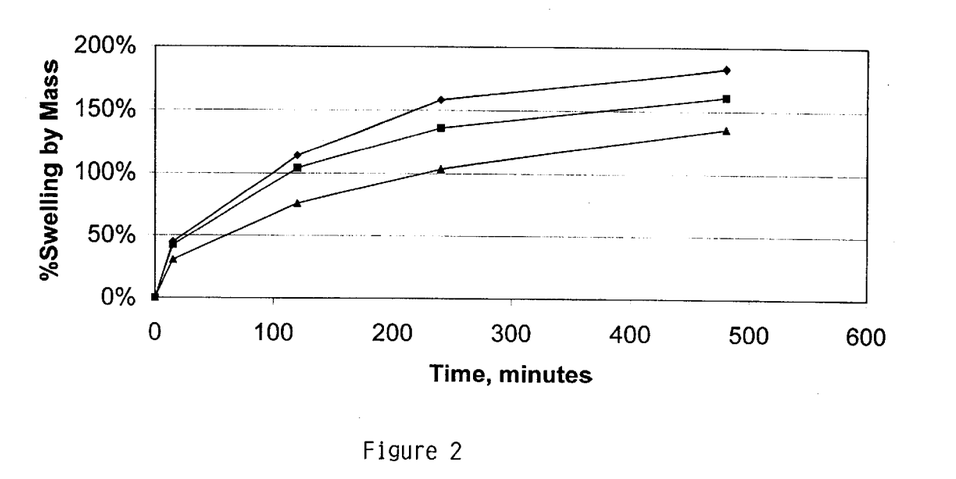
FIG. 2 is a plot showing the swelling profile of ciprofloxacin hydrochloride tablets on a mass basis in a gastric environment over time, offering the same comparison as the preceding figures.

The swelling profiles, expressed as a percent mass increase, were determined using the same conditions as those used in obtaining the dissolution profiles. The results are shown in FIG. 2 (mass swelling). The diamonds in the figure represent Lot A, the squares represent Lot B, and the triangles represent Lot C, as in FIG. 1. FIG. 2 demonstrates that the combination of HPMC and PEO shows higher swelling than HPMC alone, and thus the combination of polymers retains the good swelling characteristics of PEO.

EXAMPLE 2

This example illustrates the preparation of tablets of gabapentin in accordance with the invention, and compares the combination of PEO and HPMC with PEO alone and HPMC alone in terms of the release profile of the drug over time in simulated gastric fluid (0.1 N HCl).

The procedures used were the same as those described in Example 1, except that gabapentin was substituted for ciprofloxacin, and no additional excipients or binders were used.

Three lots of tablets were prepared, with the compositions shown in Table 2. 1, all in weight percents (Lot E representing the combination of the present invention):

TABLE 2.1

Gabapentin Tablet Composition

| Lot | % Active | % PEO | % K100M | % M. St. |
|---|---|---|---|---|
| D | 60.0 | 39.0 | 0.0 | 1.0 |
| E | 60.0 | 24.3 | 14.7 | 1.0 |
| F | 60.0 | 0.00 | 39.0 | 1.0 |

Cumulative dissolution profiles for this diffusional tablet were obtained in the same manner as those of Example 1, except that samples were taken only at 1, 4, and 8 hours, and the dissolution medium was deionized water. The profiles, based on the theoretical percent active added to the formulation, are shown in Table 2.2 and plotted in FIG. 3, in which the diamonds represent Lot D, the squares represent Lot E, and the triangles represent Lot F.

TABLE 2.2

Gabapentin Cumulative Dissolution Profiles

| | Cumulative % Active Released | | |
|---|---|---|---|
| Lot | 1 h | 4 h | 8 h |
| D | 15.4 | 39.4 | 61.7 |
| E | 14.8 | 37.4 | 57.8 |
| F | 18.6 | 43.3 | 64.7 |

Figure 3:
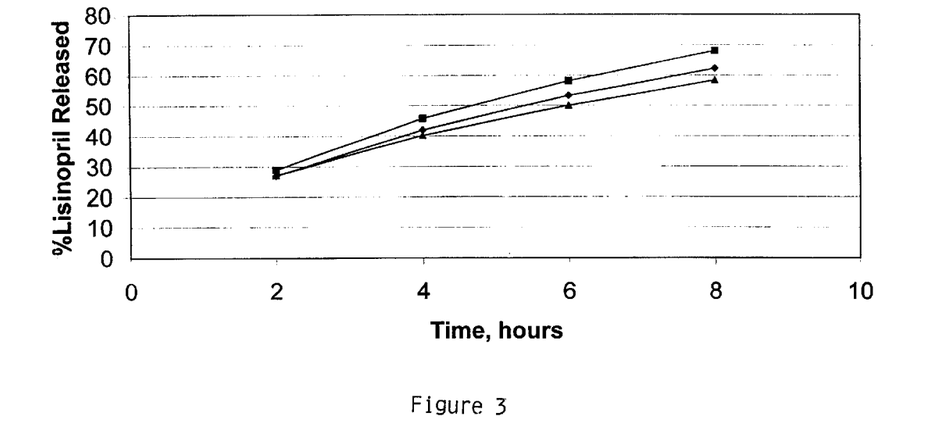
FIG. 3 is a plot showing the cumulative release of gabapentin from tablets (as a percent of the total amount originally present in each tablet) in a gastric environment over time, offering the same comparison as the preceding figures.

The dissolution profiles demonstrate that the combination of PEO and HPMC has a dissolution profile that is surprisingly less rapid than those of PEO alone and HPMC alone.

EXAMPLE 3

This example illustrates the preparation of tablets of metformin hydrochloride in accordance with the invention, and compares the combination of PEO and HPMC with PEO alone and HPMC alone in terms of the release profile of the drug over time in simulated gastric fluid (0.1 N HCl).

The procedures used were the same as those described in Examples 1 and 2, except that a grade of hydroxypropyl methyl cellulose identified as Methocel E5 premium, manufactured by Dow Chemical Company, was used in place of the PVP and the lactose monohydrate.

Three lots of tablets were prepared, with the compositions shown in Table 3.1, all in weight percents (Lot I representing the combination of the present invention). (Lots 2 and 3 were prepared on a Manesty Betapress rather than a Carver Auto C press.)

TABLE 3.1

Metformin Tablet Composition

| Lot | % Active | % E5 | % PEO | % MCC | % K100M | % M. St. |
|---|---|---|---|---|---|---|
| G | 49.67 | 3.04 | 0.00 | 0.00 | 46.33 | 0.76 |
| H | 50.00 | 1.70 | 42.55 | 5.00 | 0.00 | 0.75 |
| I | 49.97 | 1.70 | 26.50 | 4.99 | 16.08 | 0.75 |

Cumulative dissolution profiles were obtained in the same manner as those of Examples 1 and 2, except that samples were taken only at 2, 4, 6, and 8 hours. The profiles, based on the theoretical percent active added to the formulation, are shown in Table 3.2 and plotted in FIG. 4, in which the diamonds represent Lot G, the squares represent Lot H, and the triangles represent Lot I.

TABLE 3.2

Metformin Cumulative Dissolution Profiles

| | Cumulative % Active Released | | | |
|---|---|---|---|---|
| Lot | 2 h | 4 h | 6 h | 8 h |
| G | 51.0 | 70.8 | 84.6 | 95.1 |
| H | 41.4 | 61.2 | 74.9 | 85.6 |
| I | 47.8 | 68.1 | 81.0 | 88.6 |

Figure 4:
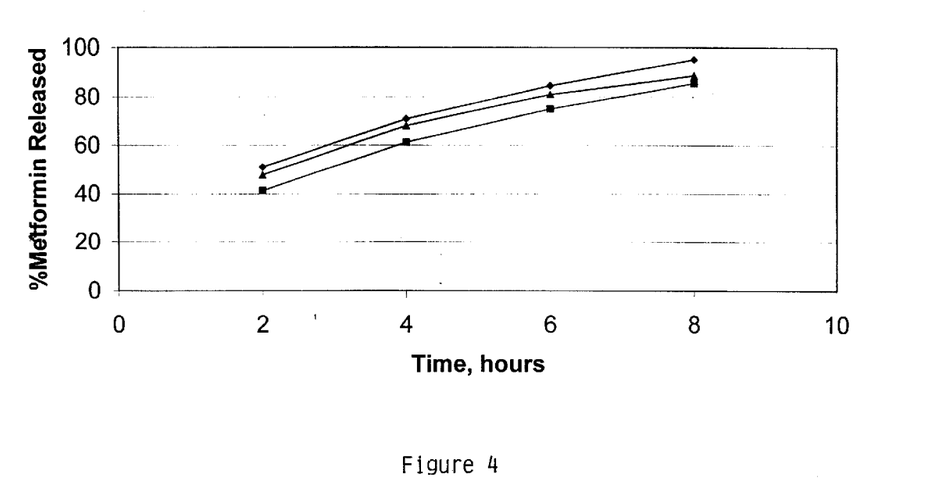
FIG. 4 is a plot showing the cumulative release of metformin hydrochloride from tablets (as a percent of the total amount originally present in each tablet) in a gastric environment over time, offering the same comparison as the preceding figures.

The dissolution profiles demonstrate that the combination of PEO and HPMC has a dissolution profile that allows extension of the drug delivery profile beyond the 90% release in 6 hours seen for HPMC alone.

Figure 5:
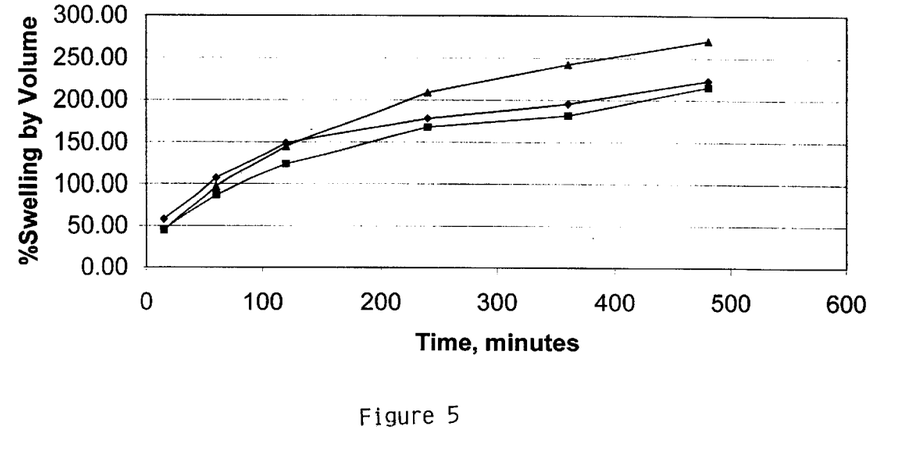
FIG. 5 is a plot showing the swelling profile of metformin hydrochloride tablets on a mass basis in a gastric environment over time, offering the same comparison as the preceding figures.

The swelling profiles, expressed as a percent mass increase, were determined using the same conditions as those used in obtaining the dissolution profiles. The results are shown in FIG. 5, in which the diamonds represent Lot I, the squares represent Lot G, and the triangles represent Lot H. Note that this is not the same notation used in the figures of the preceding examples. FIG. 5 demonstrates that PEO/HPMC has a swelling profile intermediate between that of the pure PEO and the pure HPMC.

EXAMPLE 4

This example illustrates the in vivo gastric retention of gabapentin in two formulations in accordance with the present invention, and compares this with NEURONTIN®, an immediate-release form of gabapentin available from Parke-Davis, Morris Plains, N.J., USA.

The tests were performed on beagle dogs, five each of which were administered an oral dose of either NEURONTIN® or one of two gabapentin dosage forms, all cases involving a tablet containing 300 mg of gabapentin. Table 4.1 lists the components of the two gabapentin dosage forms, GR-A and GR-B, both in accordance with the invention. Different grades of HPMC were used, Methocel K15M and Methocel K4M, the former having a viscosity of 15,000 cps as a 2% aqueous solution and the latter a viscosity of 4,000 cps as a 2% aqueous solution.

TABLE 4.1

Gabapentin Formulations Used for In Vivo Studies

|  | GR-A | | GR-B | |
| --- | --- | --- | --- | --- |
| Component | Weight % | mg per Tablet | Weight % | mg per Tablet |
| Gabapentin | 46.15 | 300 | 46.13 | 300 |
| PEO Coagulant, NF FP (low EO) | 22.61 | 147 | 0.0 | 0.0 |
| PEO 301, NF FP (low EO) | 0.0 | 0.0 | 22.63 | 147 |
| Methocel K15M, premium (USP) | 22.62 | 147 | 0.0 | 0.0 |
| Methocel K4M, premium (USP) | 0.0 | 0.0 | 22.61 | 147 |
| Avicel PH-101, NF | 7.61 | 49.5 | 7.63 | 49.5 |
| Magnesium Stearate, NF | 1.01 | 6.5 | 1.00 | 6.5 |
| Total | 100.00 | 650 | 100.00 | 650 |

Dosing was performed immediately after a meal in a non-randomized order on three separate occasions. The plasma of each dog was then sampled for the first 24 hours following the dose. The results, based on averages of five dogs for each dosage form, are shown in Table 4.2, where "IR" denotes the immediate-release NEURONTIN® tablet, "AUC" denotes area under the curve, "$C_{max}$" denotes the maximum concentration detected in the plasma, and "$t_{max}$" denotes the time at which the maximum concentration occurred.

TABLE 4.2

Pharmacokinetic Data

| Pharmacokinetic Parameter | | IR | GR-A | GR-B | (relative to the IR): GR-A | GR-B |
| --- | --- | --- | --- | --- | --- | --- |
| AUC (ng/mL-h) | Mean | 148485 | 174691 | 166940 | 118.2% | 111.8% |
|  | Std Dev | 18449 | 20496 | 35320 | N/A | N/A |
| $C_{max}$ (ng/mL) | Mean | 32039 | 20844 | 18937 | 66.9% | 60.1% |
|  | Std Dev | 5782 | 4066 | 2822 | N/A | N/A |
| $t_{max}$ (h) | Mean | 0.9 | 4.2 | 3.4 | N/A | N/A |
|  | Std Dev | 0.2 | 1.5 | 0.5 | N/A | N/A |

Figure 6:
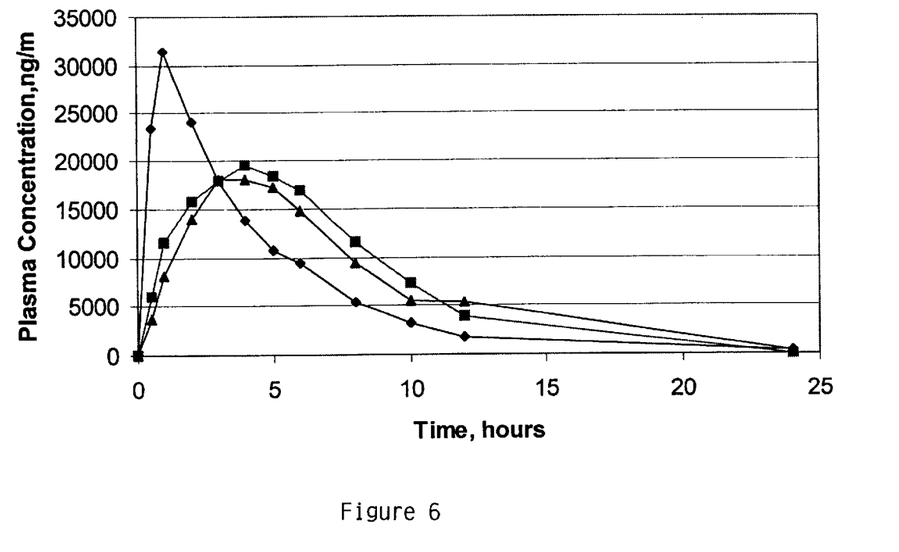
FIG. 6 is a plot of pharmacokinetic data showing the in vivo gastric retention performance of two gabapentin formulations prepared in accordance with the present invention.

The full data from which these figures are taken are shown in FIG. 6, where the diamonds denote the NEURONTIN® data, the squares the GR-A data, and the triangles the GR-B data.

The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. A controlled-release tablet for releasing a drug into at least a portion of a region defined by the stomach and the upper gastrointestinal tract, said tablet comprising a solid monolithic matrix with said drug dispersed therein, said matrix comprising a combination of poly(ethylene oxide) and hydroxypropyl methylcellulose at a weight ratio that causes said matrix to swell upon contact with gastric fluid to a size large enough to provide gastric retention, wherein;

said drug has a solubility in water that exceeds one part of said drug per ten parts of water, by weight, and wherein;

said poly(ethylene oxide) has a viscosity average molecular weight of from about 2,000,000 to about 10,000,000 daltons, and wherein said hydroxypropyl methylcellulose has a viscosity of from about 4,000 centipoise to about 200,000 centipoise, measured as a 2% solution in water.

2. A controlled-release tablet in accordance with claim 1 in which said matrix swells by at least about 20% of its original size within 30 minutes upon immersion in gastric fluid to reach at least about 90% of its maximum size within 8 hours.

3. A controlled-release tablet in accordance with claim 1 wherein said hydroxypropyl methylcellulose has a viscosity of from about 50,000 centipoise to about 200,000 centipoise, measured as a 2% solution in water.

4. A controlled-release tablet in accordance with claim 1 said poly(ethylene oxide) has a viscosity average molecular weight of from about 4,000,000 to about 7,000,000 daltons, and said hydroxypropyl methylcellulose has a viscosity of from about 80,000 centipoise to about 120,000 centipoise, measured as a 2% solution in water.

5. A controlled-release tablet in accordance with claim 1 in which said drug has a solubility in water that exceeds one part of said drug per three parts of water, by weight.

6. A controlled-release tablet for releasing a drug into at least a portion of a region defined by the stomach and the upper gastrointestinal tract, said tablet comprising a solid monolithic matrix with said drug dispersed therein, said matrix comprising a combination of poly(ethylene oxide) and hydroxypropyl methylcellulose at a weight ratio that causes said matrix to swell upon contact with gastric fluid to a size large enough to provide gastric retention, wherein;

said drug has a solubility in water that is less than one part of said drug per ten parts of water, by weight, said poly(ethylene oxide) has a viscosity average molecular weight of from about 100,000 to about 5,000,000 daltons, and said hydroxypropyl methylcellulose has a viscosity of from about 1,000 centipoise to about 100,000 centipoise, measured as a 2% solution in water.

7. A controlled-release tablet in accordance with claim 6 said poly(ethylene oxide) has a viscosity average molecular weight of from about 500,000 to about 2,500,000 daltons, and said hydroxypropyl methylcellulose has a viscosity of from about 4,000 centipoise to about 30,000 centipoise, measured as a 2% solution in water.

8. A controlled-release tablet in accordance with claim 7 in which said drug has a solubility in water ranging from about 0.05% to about 10% by weight.

9. A controlled-release tablet in accordance with claim 7 in which said drug has a solubility in water ranging from about 0.01% to about 5% by weight.

10. A controlled-release tablet in accordance with claim 1 in which the weight ratio of said poly(ethylene oxide) to hydroxypropyl methylcellulose is within the range of from about 1:2 to about 2:1.

11. A controlled-release tablet in accordance with claim 1 in which the weight ratio of said poly(ethylene oxide) and hydroxypropyl methylcellulose in combination constitute from about 15% to about 90% by weight of said dosage form.

12. A controlled-release tablet in accordance with claim 1 in which said poly(ethylene oxide) and hydroxypropyl methylcellulose in combination constitute from about 30% to about 65% by weight of said dosage form.

13. A controlled-release tablet in accordance with claim 1 in which said poly(ethylene oxide) and hydroxypropyl methylcellulose in combination constitute from about 40% to about 50% by weight of said dosage form.

14. A controlled-release tablet in accordance with claim 1 in which said drug is a member selected from the group consisting of metformin hydrochloride, losartan potassium, sodium valproate, valproic acid, and gabapentin.

15. A controlled-release tablet in accordance with claim 14 in which said drug is metformin hydrochloride.

16. A controlled-release tablet in accordance with claim 14 in which said drug is losartan potassium.

17. A controlled-release tablet in accordance with claim 9 in which said drug is ciprofloxacin.

18. A controlled-release tablet in accordance with claim 14 in which said drug is gabapentin.

19. A controlled-release tablet in accordance with claim 6 in which said matrix swells by at least about 20% of its original size within 30 minutes upon immersion in gastric fluid to reach at least about 90% of its maximum size within 8 hours.

* * * * *